United States Patent [19]

Schobel

[11] Patent Number: 4,568,560

[45] Date of Patent: Feb. 4, 1986

[54] ENCAPSULATED FRAGRANCES AND FLAVORS AND PROCESS THEREFOR

[75] Inventor: Alexander M. Schobel, North Plainfield, N.J.

[73] Assignee: Warner-Lambert Company, Morris Plains, N.J.

[21] Appl. No.: 590,123

[22] Filed: Mar. 16, 1984

[51] Int. Cl.⁴ .......................... A61K 7/16; A61K 7/26
[52] U.S. Cl. ......................................... 427/3; 424/49; 426/3; 426/5
[58] Field of Search .................. 427/3; 424/49; 426/3, 426/5

[56] References Cited

U.S. PATENT DOCUMENTS

| | | | |
|---|---|---|---|
| 2,031,233 | 2/1936 | Stillwell | 424/49 |
| 2,525,072 | 10/1950 | Kearby | 424/49 |
| 2,886,444 | 5/1959 | Rosenthal et al. | 99/135 |
| 2,886,446 | 5/1959 | Kramer et al. | 99/135 |
| 3,011,949 | 12/1961 | Bilotti | 167/82 |
| 3,201,353 | 8/1965 | Corben | 252/316 |
| 3,761,286 | 9/1973 | Shepard et al. | 99/135 |
| 3,850,838 | 11/1974 | Guckenberger et al. | 252/363.5 |
| 3,857,964 | 12/1974 | Yolles | 426/3 |
| 3,909,444 | 9/1975 | Anderson et al. | 427/3 |
| 3,920,849 | 11/1975 | Marmo et al. | 426/3 |
| 3,930,026 | 12/1975 | Clark | 426/3 |
| 3,957,964 | 5/1976 | Grimm | 424/10 |
| 3,962,463 | 6/1976 | Witzel | 426/5 |
| 3,985,913 | 10/1976 | Johnson et al. | 426/650 |
| 4,123,382 | 10/1978 | Morse et al. | 427/3 |
| 4,220,552 | 9/1980 | Hitchcock | 252/316 |
| 4,238,475 | 12/1980 | Witzel | 424/48 |
| 4,287,221 | 9/1981 | Tonedachi et al. | 427/3 |
| 4,316,915 | 2/1982 | Friello et al. | 426/5 |
| 4,423,030 | 12/1983 | Hayes et al. | 424/49 |
| 4,427,116 | 1/1984 | Brown | 424/49 |

FOREIGN PATENT DOCUMENTS 81392918 11/1981 European Pat. Off. .

*Primary Examiner*—Ronald W. Griffin
*Attorney, Agent, or Firm*—Gary M. Nath; Charles A. Gaglia, Jr.

[57] ABSTRACT

Process for preparing a controlled release encapsulated active agent by encapsulating the active agent in a coating composition comprising a water insoluble film forming composition, an enteric compound and a plasticizer for the film forming composition.

19 Claims, No Drawings

ENCAPSULATED FRAGRANCES AND FLAVORS AND PROCESS THEREFOR

FIELD OF THE INVENTION

This invention relates to a method for encapsulating fragrances and flavors. In particular it relates to the encapsulation of fragrances and flavors which have a controlled rate of release. Specifically it relates to an encapsulation method utilizing as the encapsulating medium a water insoluble film former in conjunction with an enteric composition.

BACKGROUND OF THE INVENTION

Flavors are used as adjunctives in many food and non-food products. Typically, flavors are added to confections, chewing gums, dentifrices, and so forth. More recently the application of encapsulating techniques has been applied to flavors to prolong, delay, or otherwise enhance the flavor agent's perception by the user of the product containing it.

U.S. Pat. No. 3,957,964 teaches a dentifrice containing encapsulated flavors wherein various material and synthetic polymers are used as the encapsulating medium for the polymer.

Slow release flavors entrapped in edible gels are disclosed for use in chewing gums in U.S. Pat. No. 3,920,849. Similarly, U.S. Pat. No. 3,761,286 teaches the use of encapsulated flavors in chewing gum, toothpaste and foods. The encapsulating medium is a hydroxymethyl methacrylate.

Other approaches to the encapsulation of flavors for delayed or sustained release are known to the art. For example, U.S. Pat. No. 3,201,353 discloses microinclusion containing flavors in chewing gums. U.S. Pat. No. 3,011,949 utilizes liquid sugar for coating solid particles of flavor and uses the dried, pulverized flavor material in chewing gum. Other techniques have utilized gelatin-encapsulated flavors (U.S. Pat. No. 2,886,446) and gelatin-concentrated flavors (U.S. Pat. No. 2,886,444) for use in chewing gums.

In addition to gelatin, the art discloses as encapsulating media gum arabic, ethyl cellulose modified starches, starch hydrolysates, hydrophilic colloids or combinations thereof; see for example U.S. Pat. Nos. 3,850,838; 3,930,026; 3,962,463; and 4,316,915. Generally, the teachings relating to hydrophillic colloids describe the absorption of flavors onto hydrocolloids or spray drying the flavors in an aqueous hydrocolloid/flavor matrix.

Calcium alginate is disclosed as a coating material for flavor particles in U.S. Pat. No. 3,857,964. Other patents which disclose the use of alginates as an encapsulating medium are U.S. Pat. Nos. 3,985,913 and 4,238,475.

European patent application No. 81,392,918.3 discloses a method for preparing calcium alginate fibers which are alleged to be useful in encapsulating flavors.

A delayed release sodium fluoride formula encapsulated in a pretreated ethyl cellulose is taught in U.S. Pat. No. 4,220,552. The ethyl cellulose is hydrochloric acid treated prior to use.

SUMMARY OF THE INVENTION

It has surprisingly been found that a fragrance or flavoring having a controlled release rate can be prepared by encapsulating the fragrance or flavoring in a coating comprising a water insoluble film former and an enteric composition. The enteric composition is water soluble in solutions at a pH of 5.50 or greater.

The preferred film former is ethylcellulose, and the preferred enteric composition is an acrylic polymer. The coating can be applied from an emulsion of the coating material by spray coating in a fluidized bed of the material to be encapsulated.

DETAILED DESCRIPTION

This invention relates to a method of preparing slow release flavoring agents and fragrances. In particular it relates to a process of encapsulating flavoring agents or fragrances, and the product prepared by the process. The flavoring agents and fragrances of this invention have application in denture cleanser compositions.

In the practice of this invention a solid particulate flavoring agent or fragrance is encapsulated with a film of an acrylic polymer and ethylcellulose. The encapsulation is accomplished utilizing a fluidized bed of the flavoring agent or fragrance.

Generally, flavors and fragrances in foods, chewing gums, denture compositions and so forth, are oils. These flavor or fragrance oils can be converted to a dry state by preparing compositions known in the art as spray dried flavors or fragrances. Spray dried flavors and fragrances are prepared by dissolving in water a solid carrier for the flavor or fragrance oils. The oil is then added to the water solution of carrier with high shear mixing in order to disperse the oil. The dispersion of oil in carrier solution is then spray dried.

Any water soluble edible composition may be utilized as the carrier. Generally, however, the carrier is maltodextrin. The spray dried flavor or fragrance can comprise up to about 30% by weight of flavor or fragrance oil based on carrier plus oils. The spray dried flavors or fragrances, preferably comprise about 15% to about 25% flavor or fragrance oil. The term "flavoring agent" as used in the specification and claims means a solid, particulate, water soluble composition having incorporated therein a flavor oil. The preferred method of incorporating the flavor oil into the flavoring agent is by the aforedescribed spray drying technique. The preparation of spray dried flavors is well known in the art and does not form a part of this invention.

Generally, spray dried flavors and fragrances are of a fine particle size. While it is possible to utilize such fine particle size flavoring agents or fragrance, it is preferred that the flavoring agent or fragrance, have a particle size of about 20 mesh to about 50 mesh (U.S. standard stainless steel mesh); preferably the mesh size is −20+50. The appropriate particle size range can be selected by sieving through a 20 mesh screen and utilizing material which collects on a 50 mesh screen. At particle sizes substantially smaller than 50 mesh the particles have too large a surface area and encapsulation becomes uneconomical because of the high surface area of the particle, resulting in the use of large quantities of encapsulating material. Particles of greater than 20 mesh create problems in the feeder of tableting machines for denture cleansing compositions.

In order to achieve the flavor or fragrance release rates desired in the practice of this invention the encapsulating coating composition comprises about 10% to about 25% by weight based on the total weight of encapsulated flavoring agent or fragrance, preferably about 15% to about 20% by weight. Below 10% by weight of coating the release rate will be too fast. Above 25% by weight of coating the release rate will be too slow for practical use in denture cleansing compositions.

In the practice of this invention the coating composition in a carrier vehicle is sprayed into the inlet stream of a fluidized bed in which the flavoring agent or fragrance particles are fluidized. The coating can be applied either from a solution or an emulsion. Preferably, water based emulsions are utilized to avoid health and fire hazards as well as recovery problems associated with the use of organic solvent solutions. The solids content of the vehicle used for the coating can be about 8% to about 30% by weight based on the total weight of vehicle plus coating material, preferably about 10% to about 25% by weight, more preferably about 15% to about 20% by weight. Below 8% solids inordinately long process times are required to apply coatings of a suitable thickness. At higher solids contents, that is in excess of about 30% by weight the solution or emulsion is too viscous and coating operations may show polymer incompatabilities and are therefor not uniform.

A plasticizer is required in the coating composition in order to ensure good film forming characteristic. Excessive amounts of plasticizer result in stickiness of the coating and agglomeration of coated particles. Too low a level of plasticizer results in discontinuous coatings with, as a consequence, immediate release of flavoring agent or fragrance in the solution in which it is used. While the preferred range of plasticizer will depend on the specific film forming material utilized, generally, about 18% to about 40% by weight based on the film former solids is used, preferably about 20% to about 30% (w/w). It should be noted that reference to coating weight includes film former, plasticizers and adjunctives which may be included in the coating formulation.

The type of plasticizer used will depend on the selection of the film former. Specific plasticizers are normally recommended by the film former supplier; and no advantage is seen in deviating from those recommendations. Where the film former is ethylcellulose the preferred plasticizer is dibutyl sebacate. Triethyl citrate can also be used.

The film former must not be water soluble. Since, the pH of denture cleansing compositions is usually at least 7.0 and preferably about 7.5 to about 11.0, for example, 9.0 to 10.0, the film former must not be solubilized by basic solutions. While the film former must be water insoluble it must be permeable with respect to water. Preferably the film former is swelled by water. The preferred film former is ethylcellulose.

A class of polymeric compounds used in the preparation of pharmaceutical capsules is known as enteric coatings. They are so called because they dissolve in the intestinal fluids which have a relatively high pH as compared to the very acidic stomach fluids in which the coatings are insoluble. As used in the specification and claims the term "enteric composition" means a polymer or compound which is normally water insoluble but is rendered water soluble at pH's of 5.5 or greater. Preferably a pH of at least 7.0 is required to solubilize the enteric compositions of this invention.

Typical of enteric compositions are copolymers of acrylic acetate and vinyl alcohol the ratio of acetate to alcohol groups is 1:1. The structure of these polymers is:

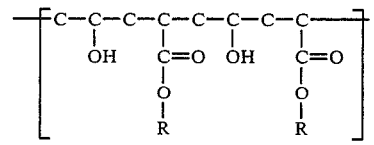

Where R is an alkyl group of about 1 to about 10 carbon atoms. Preferably R is a $C_1$–$C_4$ alkyl radical. Other enteric compositions include polyvinylbutyrate and polyvinylphthalate.

Enteric compositions are incorporated into the film former coating in order to control the rate of release of flavoring agent or fragrance. The weight ratio of film former to enteric compound is about 5:1 to about 0.5:1 preferably about 1.5:1 to about 1:1. At a weight ratio of greater than 5:1 there is insufficient enteric compound in the film and the rate of flavor release is too slow. At a ratio of less than 0.5:1.0 the rate of release of flavor is too rapid and approaches that of where no coating is used.

A particularly preferred film former suitable for use in the process of this invention is ethylcellulose when utilizing as the plasticizer dibutyl sebacate.

Both the ethylcellulose emulsion and acrylic latex dispersion are available commercially at a 30% (w/w) solids content. A plasticizer for ethylcellulose, dibutyl sebacate, is available as a 100% (w/w) active material.

Spray dried flavors and fragrances are generally available as fine powders, that is less than 100 mesh. In order to utilize these products it is preferred that they be granulated to provide particles in the 20 to 50 mesh range.

Methods of granulation are well known in the art. The particular method used in the practice of this invention utilizes a rotary mixer wherein an ethanol/water (75/25 v/v) solution is added into the powder mix and blended until a uniformly wet granulation develops. The method of granulation is not critical. In the practice of this invention about 5% to about 15% by weight of methylcellulose is added to the spray dried flavor as a granulation aid. Preferably about 8% to about 12% of methycellulose based on the weight of methylcellulose plus spray dried flavor is used.

In preparing the granulation about 50 to about 70 grams of an ethanol/water solution (75/25 v/v) per 100 grams of flavoring agent is added into the flavoring agent mix. The granulated material is then wet sceened through a 20 mesh screen, oven dried and re-sieved. All material passing through a 20 mesh screen and collected on a 50 mesh screen is reserved and the remainder is discarded or subsequently used in the granulation of fines.

The flavor oils which can be incorporated into the spray dried flavor to form the flavoring agent of this invention include the well known flavor oils utilized in processed foods, gums and confectionary compositions. Both synthetic and natural flavor oils derived from plants, leaves, flowers, fruits and so forth and combinations thereof may be utilized in the practice of this invention. Illustrative, non-limiting examples of these flavorings include spearmint oil, cinnamon oil, oil of wintergreen (methylsalicylate) and peppermint oils. Synthetic and natural fruit flavors are also useful including citrus oils, for example, lemon, orange, lime and grapefruit; fruit essences including apple, strawberry, cherry, pineapple, and the various flavorings such as aldehydes and esters including cinnamyl acetate, cinnamaldehyde, citral diethyl acetal, dihydrocarvyl acetate, eugenyl formate, p-methylamisol, and so forth. Generally, any flavoring such as those described in *Chemicals Used in Food Processing*, pub. 1274 by the National Academy of Sciences, pages 49-53 and 63-258 may be used.

Fragrances generally comprise natural and synthetic oils which give off a characteristic pleasant odor. Illustrative non-limiting examples of fragrances of this invention are spearmint, peppermint, cloves, and so forth.

The term "fragrance agent" as used in the specification and claims means the fragrance oils in a spray dried particulate form as heretofore described.

The encapsulated flavoring agent and fragrances of this invention may be used advantageously in denture cleansing compositions, chewing gums, denture adhesives, processed foods and confectionaries. The amount of flavoring agent, or fragrance agents employed is normally a matter of preference and will be determined by such factors as flavor, or fragrance type and the strength desired. In general, about 0.05% to about 3.5% by weight of encapsulated flavoring agent based on the overall composition is used, preferably about 0.5 to about 2.5% by weight, more preferably, about 0.7% to about 1.2% by weight. The fragrance agent is utilized in the same proportions set forth above for the flavoring agents.

The method of encapsulation utilized in the practice of this invention is well known to those skilled in the art and can be accomplished with an Aeromatic STREA coater using known techniques. Those skilled in the art will recognize that the objective is to produce a dry, non-tacky coated product, and therefore, will appreciate what process parameters are required to achieve that end.

The coating is applied by spraying a solution or emulsion comprising the film former composition into the air inlet stream of a fluidized bed comprising the particles to be coated. To ensure evaporation of the vehicle the inlet air temperature should be about 20° C. to about 70° C. preferably about 40° C. to about 65° C.

Sufficient air flow is required to fluidize the particles to be coated so that a "boiling bed" condition exists. The flow rate will depend on the bed height and particle density. As those skilled in the fluidzation art will recognize, the flow rate must be sufficient so that the pressure drop through the bed exceeds the bed weight per unit area. However, excessive flow rates are to be avoided to minimize attrition of particles in the air stream. The bed diameter of the equipment utilized in the reduction to practice of this invention is about 4½ inches, and bed heights of about 2 to 8 inches were used. A flow rate of about 20 m³/hr. to about 80 m³/hr. have been found to be adequate. Preferably flow rates of about 25 m³/hr. to about 70 m³/hr. are used, more preferably the fluidization flow rate is about 30 m³/hr. to about 50 m³/hr.

The encapsulation process of this invention is more readily appreciated by reference to the following examples. All parts and percentages in the examples as well as in the specification and claims are by weight unless otherwise specified.

EXAMPLE I

Granulation

A 90/10 (w/w) blend of hydroxypropyl methylcellulose and spray dried peppermint fragrance agent was prepared and charged into the rotary mixer (approximately 0.2 Kg.). A granulating fluid comprising 75/25 ethanol/ water (v/v) was added at about 65 g. per 100 g. of fragrance agent. When all of the fluid had been added, the uniformly wet granulation was discharged and passed through a 20 mesh screen. The particles were then dried at 60° C. in a forced draft oven for about 15 minutes. The dried particles were again sieved and all material which passed through 20 mesh and was retained on a 50 mesh screen was resieved for use in coating.

EXAMPLE II

Encapsulation Process

The granulated spray dried fragrance of Example I was coated with a plasticized film of ethylcellulose and acrylic polymer using an Aeromatic STREA-1 coater. The air inlet temperature was about 60° C. and the air flow rate was 32 m³/hr. The coating solution comprising the film former (ethylcellulose), enteric composition (acrylic polymer) and plasticizer (dibutyl sebacate) was sprayed into the inlet a stream at about 2 to 3 ml/min. After addition of the coating solution the product was dried in the unit for about 15 minutes at 60° C.

The theoretical coating weight on the particles was 15.28% based on the weight of fragrance agent plus coating. Approximately 0.200 Kg of charge (spray dried fragrance) was used requiring approximately 36 grams of coating material (about 200.00 gms. of coating solution). The coating solution had the following formulation:

| Coating Solution | |
|---|---|
| Ethylcellulose latex emulsion (30% solids) | 25.0% |
| Acrylic latex dispersion (30% solids) | 25.0% |
| Dibutyl sebacate | 3.0% |
| Talc | 0.035% |
| Deionized water | 46.965% |
| | 100.00% |

The talc served to minimize particle to particle adhesion. The solution was prepared using a high shear blade mixer.

EXAMPLE III

Denture Cleansing Composition

A denture cleansing tablet was prepared utilizing the encapsulated fragrance prepared in Example II. The tablet composition was as follows:

| Component | mg/tablet |
|---|---|
| Sodium Bicarbonate | 571.00 |
| Citric Acid | 416.33 |
| Sodium Carbonate | 386.30 |
| Sodium Perborate | 300.60 |
| Tetrasodium salt of Ethylene Diamine Tetracetic Acid (EDTA) | 34.74 |
| Potassium Monopersulfate | 946.80 |
| Sodium Sulfate | 90.00 |
| Detergent | 24.00 |

| Component | mg/tablet |
| --- | --- |
| Sodium Tripolyphosphate | 117.00 |
| Lubricant | 34.00 |
| Delayed Release Fragrance (Example II) | 40.00 |
| Green color granules | 167.94 |
| Blue color granules | 40.03 |
| | 3167.74 mg/tablet |

In the above denture cleansing composition the potassium monopersulfate and sodium perborate act as bleaching agents. The EDTA and sodium tripolyphosphate are sequestering agents used to maintain a solution of the composition clear. The sodium carbonate acts to buffer the pH of the cleansing solution to about 7.2 7.5. The sodium sulfate is a filler and the bicarbonate and citric acid act as effervescent agents to break up the tablet and generate a stirring action in the solution. The foregoing denture cleansing composition is merely illustrative of the denture cleansers in which the encapsulated fragrance of this invention can be utilized. The encapsulated fragrance is suitable for use in any denture cleanser composition whether in tablet or granule form.

When the above described tablet was added to 120 ml. of water at 45° C., fragrance began to be released at about 3 minutes. Maximum fragrance was detected at about 6 minutes, and the total duration of the fragrance odor was about 15 minutes. By contrast when unencapsulated fragrance is used the odor dissipates in about 3 to 5 minutes.

It is within the scope of this invention to utilize both conventional unencapsulated fragrances and the encapsulated fragrance of this invention in the same composition in order to have both instant release of fragrance as well as a delayed release of fragrance over the entire denture cleansing cycle (about 12 to 15 min.).

Similarly, where a flavoring agent is encapsulated by the process of this invention it may be utilized in conjunction with an unencapsulated flavoring for use, for example, in chewing gum.

The term "chewing gum" as used in the specification and claims means both bubble gum and adult chewing gum. Chewing gum compositions are well known in the art and generally comprise a gum base which is an uncured elastomeric polymer, a sweetener and various adjunctives including, flavorings, softeners and emulsifiers. The term "denture" as used in the specification and claims means false teeth, dental bridges and other similar orthodontic devices. The term "denture cleansing composition" as used in the specification and claims means a solid tableted or granulated cleansing agent which is utilized in a water solution to clean dentures. Denture cleansing compositions are well known in the art and generally comprise a bleaching agent, effervescent compounds, a buffer to maintain pH at about 7.0 to about 11.0, preferably about 7.5 to 9.5; a sequestering agent to hold metal compounds, for example magnesium and heavy metals in solution in order to ensure that the denture cleansing solution is clear and other adjunctives such as flavorings, coloring agents and binders.

Chewing gum compositions and denture cleansing compositions per se do not form a part of this invention unless they have incorporated therein the encapsulating flavoring agents and/or fragrance agents of this invention.

The term "controlled release" as used in the specification and claims means release of flavor or fragrance gradually over a period of time rather than instantaneous release after the passage of a period of time.

The term "active agent" as used in the specification and claims means the flavoring agents and fragrance agents which are encapsulated by the process of this invention.

This invention being thus described, it will be obvious that the same may be varied in many ways. Such variations are not to be regarded as a departure from the spirit of scope of the invention and all such modifications are intended to be included within the scope of the claims.

What is claimed is:

1. A process for preparing a controlled release encapsulated active agent which comprises:
    encapsulating the active agent selected from the group consisting of flavoring agents and fragrances in a coating composition wherein the coating composition is applied by spray coating a coating solution or a coating emulsion of the coating composition onto the active agent said coating solution or coating emulsion comprising about 8 to about 30% (w/w) of coating composition based on the weight of emulsion or solution the coating composition comprising a water insoluble film forming composition, an enteric compound and a plasticizer for the film forming composition, wherein the weight ratio of film forming composition to enteric compound is about 5:1 to about 0.5:1, said coating composition comprising about 10% to about 25% by weight of the encapsulated active agent based on the weight of active agent plus coating, and said plasticizer comprising about 18% to about 40% by weight of the weight of the film former solids.

2. The process of claim 1 wherein the film former is ethylcellulose, the enteric compound is an acrylic polymer and the plasticizer is dibutyl sebacate.

3. The process of claim 1 wherein the plasticizer comprises about 20 to about 30% (w/w) of the film former solids.

4. The process of claim 1 wherein the coating composition comprises about 15% to about 20% by weight of the encapsulated active agent.

5. The process of claim 1 wherein the ratio of film former to enteric composition is about 1.5:1 to about 1:1.

6. The process of claim 1 wherein the active agent has a particle size range of about 20 mesh to about 50 mesh.

7. The process of claim 1 wherein the active agent is a flavoring agent.

8. The process of claim 1 wherein the active agent is a fragrance agent.

9. A composition of matter comprising an active agent selected from the group consisting of flavoring agents and fragrances said active agent being encapsulated in a continuous coating which comprises a film former, an enteric composition and a plasticizer for the film former wherein the weight ratio of film former to enteric composition is about 5:1 to about 0.5:1 said coating comprising about 10% to about 25% by weight of the encapsulated active agent, and said plasticizer comprising about 18% to about 40% by weight of the weight of the film former solids.

10. The composition according to claim 9 wherein the active agent is a flavoring agent.

11. The composition according to claim 9 wherein the active agent is a fragrance agent.

12. The composition according to claim 9 wherein the film former is ethylcellulose and the plasticizer is dibutyl sebacate.

13. The composition according to claim 9 wherein the enteric composition is an acrylic polymer.

14. The composition according to claim 9 wherein the weight ratio is about 1.5:1 to about 1:1.

15. The composition according to claim 9 wherein the coating comprises about 15% to about 20% by weight of the composition.

16. The composition according to claim 9 the plasticizer comprises about 20% to about 30% by weight of the film former solids.

17. The composition according to claim 9 wherein the active agent has a particle size range of about 20 mesh to about 50 mesh.

18. In a denture cleansing composition the improvement which comprises utilizing as a fragrance the encapsulated fragrance agent of claim 11.

19. In the chewing gum composition the improvement which comprises utilizing as a flavoring the encapsulated flavoring agent of claim 10.

* * * * *

UNITED STATES PATENT AND TRADEMARK OFFICE
CERTIFICATE OF CORRECTION

PATENT NO. : 4,568,560

DATED : February 4, 1986

INVENTOR(S) : Alexander M. Schobel

It is certified that error appears in the above-identified patent and that said Letters Patent is hereby corrected as shown below:

Column 10, line 1, Claim 16 after "claim 9" insert --wherein--.

Signed and Sealed this

Thirteenth Day of May 1986

[SEAL]

*Attest:*

DONALD J. QUIGG

*Attesting Officer*

*Commissioner of Patents and Trademarks*